(12) United States Patent
Ignat et al.

(10) Patent No.: US 10,689,313 B2
(45) Date of Patent: Jun. 23, 2020

(54) PROCESSES AND SYSTEMS FOR PURIFICATION OF 1,3-BUTADIENE

(71) Applicant: SABIC Global Technologies B.V., Bergen op Zoom (NL)

(72) Inventors: Radu Mihai Ignat, Elsloo (NL); Michael Schleger, Elsloo (NL)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/763,667

(22) PCT Filed: Oct. 17, 2016

(86) PCT No.: PCT/IB2016/056233
§ 371 (c)(1),
(2) Date: Mar. 27, 2018

(87) PCT Pub. No.: WO2017/068489
PCT Pub. Date: Apr. 27, 2017

(65) Prior Publication Data
US 2018/0273446 A1    Sep. 27, 2018

Related U.S. Application Data

(60) Provisional application No. 62/245,333, filed on Oct. 23, 2015.

(51) Int. Cl.
*C07C 7/00* (2006.01)
*B01D 3/14* (2006.01)
(Continued)

(52) U.S. Cl.
CPC .............. *C07C 7/005* (2013.01); *B01D 3/143* (2013.01); *B01D 3/4211* (2013.01); *C07C 7/04* (2013.01);
(Continued)

(58) Field of Classification Search
CPC combination set(s) only.
See application file for complete search history.

(56) References Cited

U.S. PATENT DOCUMENTS

| 4,859,286 A | 8/1989 | Kaibel et al. | ................... 203/75 |
| 7,169,267 B2 | 1/2007 | Kaibel et al. | ..................... 203/1 |

(Continued)

FOREIGN PATENT DOCUMENTS

| CN | 1474794 A | 2/2004 |
| EP | 0036735 A1 | 9/1981 |

(Continued)

OTHER PUBLICATIONS

Rahimi et al. ("Modeling and Simulation of a Divided Wall Column for 1,3 Butadiene Purification", Iranian Journal of Chemical Engineering vol. 12, No. 1 (Winter 2015/Jan. 2015), IAChE). (Year: 2015).*

(Continued)

*Primary Examiner* — Ali Z Fadhel
(74) *Attorney, Agent, or Firm* — Norton Rose Fulbright US LLP

(57) ABSTRACT

Systems for purifying 1,3-butadiene are provided. An exemplary system includes a first distillation column, a second distillation column, and interconnections between the first and second distillation columns. A first interconnection can feed a liquid stream from the second distillation column to the first, while a second interconnection can feed a gas stream from the second distillation column to the first. Processes for purifying 1,3-butadiene are also provided.

17 Claims, 1 Drawing Sheet

(51) Int. Cl.
*C07C 7/04* (2006.01)
*B01D 3/42* (2006.01)
*C07C 11/167* (2006.01)

(52) U.S. Cl.
CPC ........ *C07C 11/167* (2013.01); *B01D 2256/24* (2013.01); *B01D 2257/7022* (2013.01)

(56) References Cited

U.S. PATENT DOCUMENTS

| | | | |
|---|---|---|---|
| 8,252,150 B1 | 8/2012 | Hsu et al. | 203/50 |
| 2004/0045804 A1* | 3/2004 | Bohner | B01D 3/14 |
| | | | 203/1 |
| 2014/0296589 A1 | 10/2014 | Krupa | 585/256 |

FOREIGN PATENT DOCUMENTS

| | | |
|---|---|---|
| EP | 0780147 A2 | 6/1997 |
| RU | 2442768 C2 | 2/2012 |
| WO | WO2009092682 A3 | 7/2009 |

OTHER PUBLICATIONS

Errico et al. "Energy saving and capital cost evaluation in distillation column sequences with a divided wall column." Chemical Engineering Research and Design 87 (2009) 1649-1657.
Tututi-Avila et al. "Analysis of Multi-Loop Control Structures of Dividing-Wall Distillation Columns Using a Fundamental Model." *Processes* Feb. 2014, 180-199; doi: 10.3390/pr2010180.
Wolff et al. "Operation of Integrated Three-Product (Petlyuk) Distillation Columns." Ind. Eng. Chem. Res. 1995, 34, 2094-2103.
Written Opinion and International Search Report from PCT/IB2016/056233, dated Jan. 16, 2017, 11 pages.

\* cited by examiner

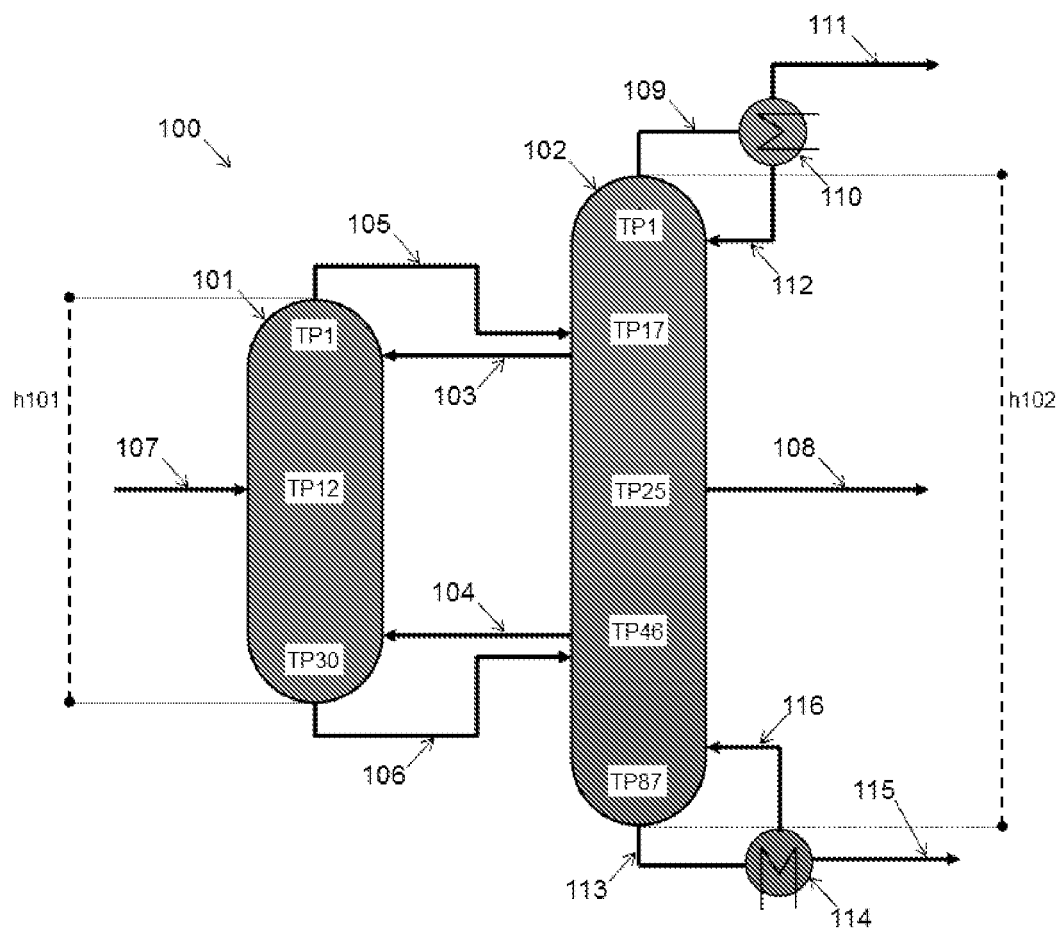

PROCESSES AND SYSTEMS FOR PURIFICATION OF 1,3-BUTADIENE

CROSS-REFERENCE TO RELATED APPLICATIONS

This application is a national phase application under 35 U.S.C. § 371 of International Application No. PCT/IB2016/056233 filed Oct. 17, 2016, which claims priority to U.S. Provisional Patent Application No. 62/245,333 filed Oct. 23, 2015. The entire contents of each of the above-referenced disclosures is specifically incorporated by reference herein without disclaimer.

FIELD

The presently disclosed subject matter relates to processes and systems for purification of 1,3-butadiene.

BACKGROUND 1,3-Butadiene is a valuable hydrocarbon. Also known as buta-1,3-diene, erythrene, and vinylethylene, it is the simplest 1,3-diene compound. 1,3-Butadiene can be used as a monomer starting material for preparation of various polymers, including synthetic rubbers. 1,3-Butadiene can be used as a feedstock in the production of adiponitrile. 1,3-Butadiene can also be used as a substrate in certain Diels-Alder reactions.

1,3-Butadiene can be obtained from different sources, including dehydrogenation of n-butane and reaction of ethanol. 1,3-Butadiene can also be isolated from mixtures of C4 hydrocarbons, e.g., C4 fractions obtained from steam cracking processes. Crude 1,3-butadiene containing about 89% to about 99% 1,3-butadiene, by weight, and smaller quantities of 1,2-butadiene, 2-butenes (both cis and trans), propyne, and/or C5 hydrocarbons can be obtained from extractive distillation methods known in the art. Crude 1,3-butadiene can be further purified to provide 1,3-butadiene of 99.6% or greater purity, by weight.

Certain methods for purification of crude 1,3-butadiene can involve two-stage distillation through two separate distillation columns. In such methods, crude 1,3-butadiene containing propyne, 1,2-butadiene, and C5 hydrocarbons, as well as other compounds, can be fed into a first distillation column. Propyne can be removed as a gas (vapor) stream from the top of the first distillation column, while a liquid stream containing 1,3-butadiene, 1,2-butadiene, and C5 hydrocarbons is passed from the first distillation column into the second distillation column. 1,3-Butadiene can then be removed as a liquid stream from the top of the second distillation column, while 1,2-butadiene and C5 hydrocarbons are removed as a liquid stream from a lower portion of the column.

A drawback of certain methods for purification of crude 1,3-butadiene can be poor performance when the crude 1,3-butadiene contains significant quantities of cis- and/or trans-2-butene. There exists a need for processes and systems for purification of 1,3-butadiene to consistently high purity, even in the presence of relatively high levels of 2-butene.

SUMMARY OF THE DISCLOSED SUBJECT MATTER

The present disclosure provides systems and processes for purifying 1,3-butadiene. In one embodiment, an exemplary system for purifying 1,3-butadiene includes a first distillation column and a second distillation column, each column having a top portion, a bottom portion, and a middle portion. The system includes a first interconnection between the top portion of the first distillation column and the top portion of the second distillation column. The first interconnection is configured to feed a liquid stream from the second distillation column to the first distillation column. The system further includes a second interconnection between the bottom portion of the first distillation column and the bottom portion of the second distillation column. The second interconnection is configured to feed a gas stream from the second distillation column to the first distillation column.

In certain embodiments, the first distillation column can be a prefractionator column having a first size and the second distillation can be a distillation column having a second size. The second size can be larger than the first size.

In certain embodiments, the system can further include a 1,3-butadiene feed line configured to feed liquid 1,3-butadiene into the first distillation column. The 1,3-butadiene feed line can be configured to feed liquid 1,3-butadiene into the middle portion of the first distillation column.

In certain embodiments, the system can further include a product outlet line configured to remove purified 1,3-butadiene from the middle portion of the second distillation column.

In certain embodiments, the first distillation column can have about 30 theoretical plates.

In one embodiment, an exemplary process for purifying 1,3-butadiene includes providing a first distillation column and a second distillation column, each column having a top portion, a bottom portion, and a middle portion. The process includes feeding liquid 1,3-butadiene into the first distillation column, removing a gas stream from the top portion of the first distillation column to the top portion of the second distillation column, and removing a liquid stream from the bottom portion of the first distillation column to the bottom portion of the second distillation column. The process further includes withdrawing a fraction of a liquid reflux in the second distillation column and feeding the fraction of the liquid reflux to the first distillation column, withdrawing a fraction of a gas phase in the second distillation column and feeding the fraction of the gas phase to first distillation column, and removing purified 1,3-butadiene from the second distillation column.

In certain embodiments, the liquid 1,3-butadiene can be crude 1,3-butadiene containing cis-2-butene and/or trans-2-butene. In certain embodiments, the purified 1,3-butadiene can have a purity of at least 99.6%, by weight.

In certain embodiments, processes for purifying 1,3-butadiene can further include removing a gas stream including propyne from the second distillation column.

In certain embodiments, processes for purifying 1,3-butadiene can further include removing a liquid stream including 1,2-butadiene, cis-2-butene, trans-2-butene, and/or C5 hydrocarbons from the second distillation column.

In certain embodiments, the pressure within the second distillation column can be between 3 bar and 8 bar. In certain embodiments, the temperature within the second distillation column can be between 30° C. and 50° C.

BRIEF DESCRIPTION OF THE DRAWINGS

FIG. 1 is a schematic diagram showing an exemplary system for purification of 1,3-butadiene in accordance with one non-limiting embodiment of the disclosed subject matter.

DETAILED DESCRIPTION

The presently disclosed subject matter provides systems and processes for purifying 1,3-butadiene. The 1,3-butadiene purified by the systems and processes of the present disclosure can be crude 1,3-butadiene. The crude 1,3-butadiene can be derived from fractionation of a C4 hydrocarbon cut. For example, crude 1,3-butadiene can be obtained from two stage extractive distillation of a C4 fraction obtained from steam cracking. Crude 1,3-butadiene can also be obtained from on-purpose 1,3-butadiene production technologies such as dehydration of n-butane. Crude 1,3-butadiene can have a purity in a range from about 89% to about 99%, by weight, e.g., 89%, 90%, 91%, 92%, 93%, 94%, 95%, 96%, 97%, 98%, or 99%, by weight. Crude 1,3-butadiene can contain various impurities, which can include 1,2-butadiene, cis-2-butene, trans-2-butene, propyne, and C5 hydrocarbons (e.g., isomers of pentane and isomers of pentene).

For the purpose of illustration and not limitation, FIG. 1 is a schematic diagram depicting an exemplary system for purifying 1,3-butadiene in accordance with one non-limiting embodiment of the disclosed subject matter. The exemplary system 100 can include a first distillation column 101 and a second distillation column 102, each column having a top portion, a bottom portion, and a middle portion. The first distillation column 101 and the second distillation column 102 can be oriented vertically, as shown in FIG. 1. The first distillation column 101 and second distillation column 102 can each have a height, denoted in FIG. 1 as h101 and h102, respectively.

By way of non-limiting example, the top portion of each column can be defined as approximately the top quarter of each column, i.e., the portion of each column 101, 102 extending from the top of the column down to one fourth (¼) of the distance from the top of the column to the bottom of the column along the height h101, h102. The middle portion of each column can be defined as approximately the next quarter of each column, i.e., the portion of each column 101, 102 extending from one quarter (¼) of the distance to two quarters (2/4) of the distance from the top of the column to the bottom of the column along the height h101, h102. The bottom portion of each column can be defined as approximately the bottom half of each column, i.e., the portion of each column 101, 102 extending from two quarters (2/4) of the distance from the top of the column to the bottom of the column along the height h101, h102 to the bottom of the column.

The top portion, bottom portion, and middle portion of each column 101, 102 can alternatively be defined in terms of the theoretical plates of each column. In certain embodiments, theoretical plates can be spaced evenly along the height of each column. As shown in FIG. 1, an exemplary first distillation column 101 has 30 theoretical plates. The first (1st), twelfth (12th), and 30th theoretical plates of the first distillation column 101 are denoted in FIG. 1 as TP1, TP12, and TP30, respectively. The top portion of the first distillation column 101 can be defined as encompassing the first (1st) theoretical plate through approximately the eighth (8th) theoretical plate. The middle portion of the first distillation column 101 can be defined as encompassing approximately the ninth (9th) theoretical plate through approximately the 16th theoretical plate. The bottom portion of the first distillation column 101 can be defined as encompassing approximately the 17th theoretical plate through the 30th theoretical plate. As shown in FIG. 1, an exemplary second distillation column 102 has 87 theoretical plates. The first (1st), 17th, 25th, 46th, and 87th theoretical plates of the second distillation column 102 are denoted in FIG. 2 as TP1, TP17, TP25, TP46, and TP87, respectively. The top portion of the second distillation column 102 can be defined as encompassing the first (1st) theoretical plate through approximately the 20th theoretical plate. The middle portion of the second distillation column 102 can be defined as encompassing approximately the 21st theoretical plate through approximately the 40th theoretical plate. The bottom portion of the second distillation column 102 can be defined as encompassing approximately the 41st theoretical plate through the 87th theoretical plate.

As shown in FIG. 1, the system 100 can further include a first interconnection 103 between the top portion of the first distillation column 101 and the top portion of the second distillation column 102. The first interconnection 103 can be configured to feed a liquid stream from the second distillation column 102 to the first distillation column 101. In other words, the first interconnection 103 can withdraw a fraction of a liquid reflux in the second distillation column 102 and feed the fraction of the liquid reflux to the first distillation column 101. The system 100 can also include a second interconnection 104 between the bottom portion of the first distillation column 101 and the bottom portion of the second distillation column 102 and can be configured to feed a gas stream from the second distillation column 102 to the first distillation column 101. In other words, the second interconnection 104 can withdraw a fraction of a gas phase in the second distillation column 102 and feed the fraction of the gas phase to the first distillation column 101.

As shown in FIG. 1, the system 100 can further include a third interconnection 105 between the top portion of the first distillation column 101 and the top portion of the second distillation column 102. The third interconnection 105 can be configured to feed a gas stream from the first distillation column 101 to the second distillation column 102. In other words, the third interconnection 105 can remove a gas stream from the top portion of the first distillation column 101 to the top portion of the second distillation column 102. The system 100 can also include a fourth interconnection 106 between the bottom portion of the first distillation column 101 and the bottom portion of the second distillation column 102. The fourth interconnection 106 can be configured to feed a liquid stream from the first distillation column 101 to the second distillation column 102. In other words, the fourth interconnection 106 can remove a liquid stream from the bottom portion of the first distillation column 101 to the bottom portion of the second distillation column 102.

As shown in FIG. 1, the system 100 can include a 1,3-butadiene feed line 107 configured to feed liquid 1,3-butadiene into the first distillation column 101. The 1,3-butadiene feed line 107 can feed 1,3-butadiene into the middle portion of the first distillation column 101. The 1,3-butadiene feed line 107 can feed 1,3-butadiene from a crude 1,3-butadiene source, e.g., crude 1,3-butadiene derived from a C4 hydrocarbon cut, as described above.

As shown in FIG. 1, the system 100 can include a product outlet line 108 configured to remove purified 1,3-butadiene from the middle portion of the second distillation column 102. The system 100 can include a top stream line 109 configured to remove a gas stream from the top portion of the second distillation column 102. The top stream line 109 can be coupled to a heat exchanger 110. The heat exchanger 110 can be a condenser adapted to cool the gas stream fed from the top stream line 109. The heat exchanger 110 can condense a fraction of low volatility components within the gas stream from the top stream line 109 and can return the low volatility components to the second distillation column 102 through a return line 112. The low volatility components returned to the second distillation column 102 can include 1,3-butadiene. Components of higher volatility within the gas stream from the top stream line 109, e.g., propyne, can remain gases after passage through the heat exchanger 110 and can be separated as a gas stream moving through a vapor outlet line 111. Propyne and other components of higher volatility can be recovered from the vapor outlet line 111. The system 100 can also include a bottom stream line 113 configured to remove a liquid stream from the bottom portion of the second distillation column 102. The bottom stream line 113 can be coupled to a heat exchanger 114. The heat exchanger 114 can warm the liquid stream fed from the bottom stream line 113. The heat exchanger 114 can vaporize a fraction of the components of higher volatility within the liquid stream from the bottom stream line 113 and can return the components of higher volatility to the second distillation column 102 through a return line 116. The components of higher volatility returned to the second distillation column 102 can include some amount of 1,3-butadiene. Low volatility components within the liquid stream from the bottom stream line 113, e.g., 1,2-butadiene, cis-butene, trans-butene, and C5 hydrocarbons, can remain liquids after passage through the heat exchanger 114 and can be separated as a liquid stream moving through a liquid outlet line 115.

In certain embodiments, one or both of the heat exchangers 110, 114 can include gas/liquid separators. In other embodiments, one or both of the heat exchangers 110, 114 can be coupled to separate gas/liquid separators. By way of non-limiting example, heat exchanger 110 can be coupled to a reflux drum, which can separate a liquid stream (e.g., a liquid stream sent through return line 112) and a gas stream (e.g., a gas stream sent through vapor outlet line 111). By way of non-limiting example, heat exchanger 114 can be a kettle- or thermosiphon-type reboiler, which can separate a liquid stream (e.g., a liquid stream sent through liquid outlet line 115) and a gas stream (e.g., a gas stream sent through return line 116).

As shown in FIG. 1, the first distillation column 101 is a prefractionator column having a first size and the second distillation column 102 is a distillation column having a second size. The second size can be larger than the first size. For example, as shown in FIG. 1, the height of the second distillation column 102, h102, can be greater than the height of the first distillation column 101, h101. In certain embodiments, the second distillation column 102 can include a condenser and reboiler for heat input while the first distillation column 101 can be operated without a condenser or reboiler. In this way, the first distillation column 101 can serve as a prefractionator column while the second distillation column 102 can serve as a main distillation column. Operation of the first distillation column 101 without a condenser or reboiler can improve energy consumption of the system 100.

One or both of first distillation column 101 and the second distillation column 102 can be equipped with one or more trays. Additionally or alternatively, one or both of first distillation column 101 and the second distillation column 102 can be packed with packing material.

In certain embodiments, the pressure within the first distillation column 101 and the second distillation column 102 can be in a range from about 3 bar to about 8 bar. Pressure within the columns 101, 102 can be adjusted such that the pressure within each column is the same. By way of non-limiting example, pressure within the columns 101, 102 can be about 3 bar, about 4 bar, about 5 bar, about 6 bar, about 7 bar, or about 8 bar. In certain embodiments, the pressure in both the first distillation column 101 and the second distillation column 102 can be about 4 bar, e.g., 3.5 bar, 3.6 bar, 3.7 bar, 3.8 bar, 3.9 bar, 4.0 bar, 4.1 bar, 4.2 bar, 4.3 bar, 4.4 bar, or 4.5 bar.

The temperatures within the first distillation column 101 and the second distillation column 102 can be the same or different. The temperatures in the top portion, middle portion, and bottom portion of each column 101, 102 can be different. For example, the temperature of the top portion of the second column 102 can be lower than temperature of the bottom portion of the second column 102. In certain embodiments, the temperature within the first distillation column 101 can be in a range between about 20° C. and about 70° C. The temperature within the second distillation column 102 can be in a range between about 20° C. and about 70° C. In certain embodiments, the temperature within the second distillation column 102 can be between about 30° C. and about 50° C. By way of non-limiting example, the temperature within the top portion of the second distillation column 102 can be about 35° C. (e.g., 34° C.) and the temperature within the bottom portion of the second distillation column 102 can be about 45° C. (e.g., 46° C.).

The first distillation column 101, the second distillation column 102, and the interconnections 103, 104, 105, 106 can be described as constituting a thermally coupled distillation system.

In one embodiment, an exemplary process for purifying 1,3-butadiene through the system 100 of FIG. 1 includes providing a first distillation column 101 and a second distillation column 102, each column having a top portion, a bottom portion, and a middle portion, as defined above. Liquid 1,3-butadiene can be fed into the first distillation column 101 through the 1,3-butadiene feed line 107. 1,3-Butadiene and various other components present can then be refluxed in the first distillation column 101. A gas stream can be removed from the top portion of the first distillation column 101 to the top portion of the second distillation column 102 through the third interconnection 105. The gas stream removed through the third interconnection 105 can include propyne and 1,3-butadiene (e.g., about 5-15% propyne and up to about 85%-95% 1,3-butadiene, by weight). A liquid stream can be removed from the bottom portion of the first distillation column 101 to the bottom portion of the second distillation column 102 through the fourth interconnection 106. The liquid stream removed through the fourth interconnection 106 can include 1,3-butadiene (e.g., up to about 85-95% 1,3-butadiene, by weight). 1,3-Butadiene and various other components present can then be refluxed in the second distillation column 102. A fraction of the liquid reflux in the second distillation column 102 can be withdrawn through the first interconnection 103 and fed to the first distillation column 101. The liquid stream withdrawn through the first interconnection 103 can include 1,3-butadiene (e.g., about 90%, by weight, or greater). The fraction of the liquid reflux withdrawn can be in a range from about 5% to about 80% of the liquid reflux, e.g., about 5%, about 10%, about 15%, about 20%, about 25%, about 30%, about 35%, about 40%, about 45%, about 50%, about 55%, about 60%, about 65%, about 70%, about 75%, or about 80%. A fraction of the gas phase in the second distillation column 102 can be withdrawn through the second interconnection 104 and fed to the first distillation column 101. The gas stream withdrawn through the second interconnection 104 can include 1,3-butadiene as well as other components, including 1,2-butadiene, cis-2-butene, trans-2-butene, and C5 hydrocarbons. The gas stream withdrawn through the second interconnection 104 can include 1,3-butadiene in an amount of about 90%, by weight, or greater. The fraction of the gas phase withdrawn can be in a range from about 5% to about 80% of the gas phase, e.g., about 5%, about 10%, about 15%, about 20%, about 25%, about 30%, about 35%, about 40%, about 45%, about 50%, about 55%, about 60%, about 65%, about 70%, about 75%, or about 80%. Purified 1,3-butadiene can be removed as a liquid stream from the second distillation column 102 through the product outlet line 108.

Processes for purifying 1,3-butadiene can further include removing a gas stream including propyne from the second distillation column 102 through the vapor outlet line 111. Propyne can be recovered and, if desired, can be further purified according to methods known in the art, e.g., further distillation.

Processes for purifying 1,3-butadiene can further include removing a liquid stream including 1,2-butadiene, cis-2-butene, trans-2-butene, and/or C5 hydrocarbons (e.g., isomers of pentane and isomers of pentene) from the second distillation column 102 through the liquid outlet line 115. These compounds can be recovered and, if desired, can be separated from one another and further purified according to methods known in the art, e.g., further distillation.

The purity of the 1,3-butadiene obtained from the processes and systems of the present disclosure can be greater than 99%, by weight. For example, in certain embodiments the purity of the purified 1,3-butadiene can be 99%, 99.1%, 99.2%, 99.3%, 99.4%, 99.5%, 99.6%, 99.7%, 99.8%, 99.9%, or greater than 99.9%, by weight. The purified 1,3-butadiene obtained from the processes and systems of the present disclosure can be used for applications demanding high purity 1,3-butadiene, e.g., polymerization.

The processes and systems of the presently disclosed subject matter can have numerous advantages over certain existing technologies, including improved reliability and consistency of the purified 1,3-butadiene product. The processes and systems of the present disclosure can also consume less energy and require less distillation equipment, which can improve efficiency and reduce costs.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the disclosed subject matter is not intended to be limited to the particular embodiments described in the specification. Accordingly, the appended claims are intended to include within their scope such alternatives.

EXAMPLES

The following non-limiting examples are included purely by way of illustration of the presently disclosed subject matter. The following examples are the results of steady-state computer simulations conducted with ASPENTECH® ASPEN PLUS® versions 2006.5 and V8.2.

Example 1—Parameters within an Exemplary System

A system 100 in accordance with FIG. 1 is provided. The parameters of the system 100 are set forth in Table 1.

TABLE 1

| Parameters | Value |
| --- | --- |
| Operating pressure, bar | 3.9 |
| Number of stages (theoretical plates) of first distillation column 101 (prefractionator column) | 30 |
| Number of stages (theoretical plates) of second distillation column 102 (main distillation column) | 87 |
| Feed stage, first distillation column 101 (prefractionator column) | 12 |
| Product withdrawal stage, second distillation column 102 (main distillation column) | 25 |
| Liquid and vapor stream connection stages, second distillation column 102 (main distillation column) | 17, 46 |
| Reflux rate through second distillation column 102 (main distillation column), kg/h | 64677 |
| Liquid split ratio, second distillation column 102 (main distillation column), kg/kg | 0.2 |
| Vapor split ratio, second distillation column 102 (main distillation column), kg/kg | 0.26 |
| Reboiler duty, kw | 6856 |
| Condenser duty, kw | −6841 |

The reboiler duty and condenser duty values in Table 1 measure energy input into the second distillation column 102 (main distillation column). These values indicate that systems and processes in accordance with the presently disclosed subject matter can be energy efficient.

Example 2—Process for Purifying 1,3-Butadiene

A stream of 15750 kg/h crude 1,3-butadiene is fed into a system 100 in accordance with FIG. 1. The stream of crude 1,3-butadiene has the composition presented in Table 2.

TABLE 2

| Component | Concentration (weight %) |
| --- | --- |
| 1,3-butadiene | 99.0 |
| propyne | 0.003 |
| cis-2-butene | 0.9 |
| trans-2-butene | 0.06 |
| 1,2-butadiene | 0.017 |
| C5 hydrocarbons | 0.02 |

Crude 1,3-butadiene is fed in liquid form via a 1,3-butadiene feed line 107 into the 12th theoretical plate of a first distillation column 101, which has 30 theoretical plates. The top vapor stream of the first distillation column 101 is fed into the 17th theoretical plate of a second distillation column 102 via a third interconnection 105. The bottom liquid stream of the first distillation column 101 is fed into the 46th theoretical plate of the second distillation column 102 via a fourth interconnection 106. Part of a liquid reflux from the second distillation column 102 is withdrawn from the 17th theoretical plate and fed to the 1st theoretical plate of the first distillation column 101 via a first interconnection 103. The ratio of the liquid split (i.e., the fraction of the liquid reflux withdrawn) is 0.2 kg/kg. Within the bottom portion of the second distillation column 102, a vapor (gas) stream is withdrawn from the 46th theoretical plate and fed to the 30th theoretical plate of the first distillation column 101 via a second interconnection 104. The vapor split (i.e., the fraction of the gas phase withdrawn) is 0.26 kg/kg. Purified 1,3-butadiene is withdrawn from the second distillation column 102 as a side stream from the 25th theoretical plate via a product outlet line 108 in the amount of 15,655 kg/h. The purified 1,3-butadiene has a purity of 99.6%, by weight. Propyne and other low volatility components are removed from the second distillation column 102 as a gas stream via a top stream line 109 and vapor outlet line 111, in the amount of 35 kg/h. C5 hydrocarbons, 1,2-butadiene, cis-butene, trans-butene, and other heavy components are removed from the second distillation column 102 as a liquid stream via a bottom stream line 113 and liquid outlet line 115, in the amount of 60 kg/h.

The pressure within both columns 101, 102 is 4 bar. The first distillation column 101 is operated at a temperature within the top portion of 37° C. and a temperature within the bottom portion of 42° C. The second distillation column 102 is operated at a temperature within the top portion of 34° C. and a temperature within the bottom portion of 46° C.

The invention claimed is:

1. A system for purifying 1,3-butadiene, comprising:
   a first distillation column and a second distillation column, each column having a top portion, a bottom portion, and a middle portion;
   a first interconnection between the top portion of the first distillation column and the top portion of the second distillation column, wherein the first interconnection is configured to feed a liquid stream from the second distillation column to the first distillation column;
   a second interconnection between the bottom portion of the first distillation column and the bottom portion of the second distillation column, wherein the second interconnection is configured to feed a firstgas stream from the second distillation column to the first distillation column;
   a top stream line configured to remove a second gas stream from the top portion of the second distillation column, wherein the top stream line is coupled to a heat exchanger;
   a vapor outlet line operatively connected to the heat exchanger to recover high volatility componentsfrom the second gas stream;
   a feed line forcrude 1,3-butadiene to the first distillation column;
   a product outlet line for purified 1,3-butadiene from the second distillation column;
   a third interconnection between the top of the first distillation column and the top of the second column to feed a gas stream from the first column to the second column; and
   a fourth interconnection between the bottom of the first column to the bottom of the second column to feed liquid from the bottom of the first column to the bottom of the second column;
   wherein the second distillation column comprises about 87 theoretical plates; and
   wherein the first distillation column has 30 theoretical plates.

2. The system of claim 1, wherein the first distillation column is a prefractionator column having a first size and the second distillation column is a distillation column having a second size, wherein the prefractionator does not comprise a condenser or a reboiler, wherein the distillation column comprises a condenser and a reboiler; wherein the second size is larger than the first size.

3. The system of claim 1, wherein the 1,3-butadiene feed line is configured to feed liquid 1,3-butadiene into the middle portion first distillation column.

4. A process for purifying 1,3-butadiene utilizing the system of claim 1, comprising:
   feeding a crude liquid 1,3-butadiene into the first distillation column through the 1,3-butadiene feed line;
   removing the gas stream from the top portion of the first distillation column and feeding itto the top portion of the second distillation column through the third interconnection;
   removing liquid from the bottom portion of the first distillation column and feeding itto the bottom portion of the second distillation column through the fourth interconnection;
   withdrawing a fraction of a liquid reflux in the second distillation column and feedingthe fraction of the liquid reflux as the liquid stream to the first distillation column through the first interconnection, wherein the fraction of the liquid reflux withdrawn is in a range from about 20% to about 80% of the liquid reflux;
   withdrawing a fraction of a gas phase in the second distillation column and feedingthe fraction of the gas phase to the first distillation column as the firstgas stream through the second interconnection; and
   removing purified 1,3-butadiene from the product outlet line of the second distillation column.

5. The process of claim 4, wherein the liquid 1,3-butadiene is crude 1,3-butadiene comprising at least one compound selected from the group consisting of cis-2-butene and trans-2-butene.

6. The process of claim 5, wherein the pressure within the second distillation column is between 3 bar and 8 bar and the temperature within the second distillation column is between 30° C. and 50° C.

7. The process of claim 5, further comprising removing a gas stream comprising propyne from the second distillation column.

8. The process of claim 4, wherein the purified 1,3-butadiene has a purity of at least 99.6%, by weight.

9. The process of claim 8, wherein the pressure within the second distillation column is between 3 bar and 8 bar and the temperature within the second distillation column is between 30° C. and 50° C.

10. The process of claim 8, further comprising removing a gas stream comprising propyne from the second distillation column.

11. The process of claim 10, further comprising removing a liquid stream comprising at least one compound selected from the group consisting of 1,2-butadiene, cis-2-butene, trans-2-butene, and C5 hydrocarbons from the second distillation column.

12. The process of claim 4, further comprising removing a gas stream comprising propyne from the second distillation column.

13. The process of claim 12, wherein the pressure within the second distillation column is between 3 bar and 8 bar and the temperature within the second distillation column is between 30° C. and 50° C.

14. The process of claim 13, further comprising removing a liquid stream comprising at least one compound selected from the group consisting of 1,2-butadiene, cis-2-butene, trans-2-butene, and C5 hydrocarbons from the second distillation column.

15. The process of claim 4, further comprising removing a liquid stream comprising at least one compound selected from the group consisting of 1,2-butadiene, cis-2-butene, trans-2-butene, and C5 hydrocarbons from the second distillation column.

16. The process of claim 15, wherein the pressure within the second distillation column is between 3 bar and 8 bar and the temperature within the second distillation column is between 30° C. and 50° C.

17. The process of claim 4, wherein the pressure within the second distillation column is between 3 bar and 8 bar and the temperature within the second distillation column is between 30° C. and 50° C.

* * * * *

UNITED STATES PATENT AND TRADEMARK OFFICE
CERTIFICATE OF CORRECTION

PATENT NO.       : 10,689,313 B2
APPLICATION NO.  : 15/763667
DATED            : June 23, 2020
INVENTOR(S)      : Radu Mihai Ignat and Michael Schleger Page 1 of 1

It is certified that error appears in the above-identified patent and that said Letters Patent is hereby corrected as shown below:

In the Claims

In Column 9, Claim 1, Line 43, please delete "componentsfrom" and replace with "components from"
In Column 9, Claim 1, Line 45, please delete "forcrude" and replace with "for crude"
In Column 10, Claim 4, Line 9, please delete "itto" and replace with "it to"
In Column 10, Claim 4, Line 14, please delete "itto" and replace with "it to"
In Column 10, Claim 4, Line 18, please delete "feedingthe" and replace with "feeding the"
In Column 10, Claim 4, Line 24, please delete "feedingthe" and replace with "feeding the"
In Column 10, Claim 4, Line 25, please delete "firstgas" and replace with "first gas"

Signed and Sealed this
Fifteenth Day of December, 2020

Andrei Iancu
*Director of the United States Patent and Trademark Office*